United States Patent [19]

Wotzka et al.

[11] Patent Number: 5,452,081
[45] Date of Patent: Sep. 19, 1995

[54] TEXTURE MATCHING DEVICE

[75] Inventors: Friedrich Wotzka, White Plains, N.Y.; Richard C. Bartell, West Hartford, Conn.

[73] Assignee: International Business Machines Corporation, Armonk, N.Y.

[21] Appl. No.: 321,490

[22] Filed: Oct. 12, 1994

[51] Int. Cl.[6] .............................................. G01J 3/52
[52] U.S. Cl. .................................... 356/243; 356/423
[58] Field of Search .......... 356/243, 421, 422, 423–424

[56]  References Cited

U.S. PATENT DOCUMENTS

| | | | |
|---|---|---|---|
| 241,655 | 5/1881 | Heeren | 356/423 |
| 2,364,609 | 12/1944 | Almquist | 356/243 |
| 4,112,594 | 9/1978 | Impastato | 356/423 X |

Primary Examiner—Vincent P. McGraw
Attorney, Agent, or Firm—Steven B. Phillips

[57] ABSTRACT

Visual inspection device for inspecting the finish on manufactured goods. A plurality of samples are joined together in a substantially flat, substantially disk-like shape for easy viewing. The device includes a viewing hole in the center so that the surface being inspected can be viewed both through the hole and on the outside of the device, thus making comparisons by eye more accurate. The device optionally includes radial slots so that multiple devices can be fastened together or a device can be fastened to another object.

8 Claims, 4 Drawing Sheets

TEXTURE MATCHING DEVICE

BACKGROUND

1. Field of the Invention

This invention relates to apparatus to aid in the quality control testing of manufactured articles. Specifically, it relates to a device to aid in determining the finish characteristics of surfaces, such as the outside surfaces of a housing for a piece of equipment or appliance.

2. Prior Art

Monitoring the color, texture and other visual characteristics of manufactured goods has always been an important part of the manufacturing arts. Although automated methods of measuring color and texture have been developed, it is often most cost effective and more accurate to determine color and/or texture of goods through visual inspection. Problems associated with visual inspection methods generally stem from the fact that human visual perception is often uncertain and subjective. In order to overcome these problems, a variety of inspection aids and color and texture matching devices have been developed.

One perception problem associated with visual inspection is especially acute when multiple finish samples are compared to an article in succession. This problem is the inability to remember how the finish of the article being tested compared to previous samples. In addition to this memory problem, the use of multiple, separate finish samples is cumbersome and expensive because the human inspector must carry or have on hand multiple samples. These problems have been solved through combining multiple visual samples, such as colors or textures, within one convenient inspection tool. For example, U.S. Pat. No. 5,160,980 to Herpichboehm et al. discloses multiple color samples in one test strip device. U.S. Pat. No. 1,293,793 to Kaddatz discloses a device for determining the quality of milk by comparing a small sample of the milk against a plurality of possible milk color samples all deposited on a single device. U.K. Patent 351,350 discloses a device for determining the texture of sheet metal in which samples of various possible textures are arranged on a long strip.

Another perception related problem with human inspections is created because lighting, shadows and positioning can change the way a person visually perceives color and texture. This problem can be alleviated through the use of samples with a viewing hole or aperture so that the finish being inspected is seen through the aperture, and if possible, next to at least two sides of the finish sample. For example, German Patent DE-2845-237 to Rath discloses a magnetic foil sample with a viewing aperture for matching the finish color on automobiles. The article "Determination of the Skin Color with the use of Perforated Munsell Color Standards", *Israel Journal Medical Science*, Jan. 5, 1965, discuses improving the accuracy of visual skin color determination by making perforations in standard skin color charts.

The perception problems with visual inspections as discussed above are magnified when one is seeking to inspect the finish texture on articles that can be manufactured in different colors. In order to maintain accuracy, the samples must be arranged and used in such a way so that only one visual characteristic varies at a time. What is needed is a convenient visual inspection device that overcomes the perception and practical problems discussed above and provides various finishes in one device.

SUMMARY

The present invention solves the problems discussed above by providing an inspection device in which a plurality of finish samples are joined together in a substantially flat, substantially rigid, disk-like shape for easy viewing. The device includes a viewing hole in the center so that the surface being inspected can be viewed both through the hole and on the outside of the device, thus making comparisons by eye more accurate.

In the preferred embodiment, the device is actually shaped like a polygon with one sample per side, so as to facilitate holding the device edgewise against the housing of a manufactured article to be inspected. This shape is preferred because it gives the user a choice of laying the inspection device flat on a surface or holding it against the side of a housing. However, the inspection device can also be made round so that it resembles an annulus. In any case, it is important that only one visual characteristic be varied from one sample panel to another so that an inspector can make accurate determinations. For example, when the surface texture is varied from one sample to the other, the color of all the samples in one device should be exactly the same. In this case, a separate device is made for each possible color, and the inspector picks the device color that matches the article to be inspected and makes a determination of the finish texture.

The inspection device can be made by fixing a plurality of substantially flat panels together edgewise to form a flat structure with a viewing hole at the center. Alternatively, it can be made by flatly affixing solid panels to a one-piece substrate of the appropriate shape. The device sometimes has optional slots protruding partly into the device and spaced evenly around the perimeter for fastening multiple devices together for convenient transportation or storage.

DETAILED DESCRIPTION OF THE PREFERRED EMBODIMENT

Figure 1:
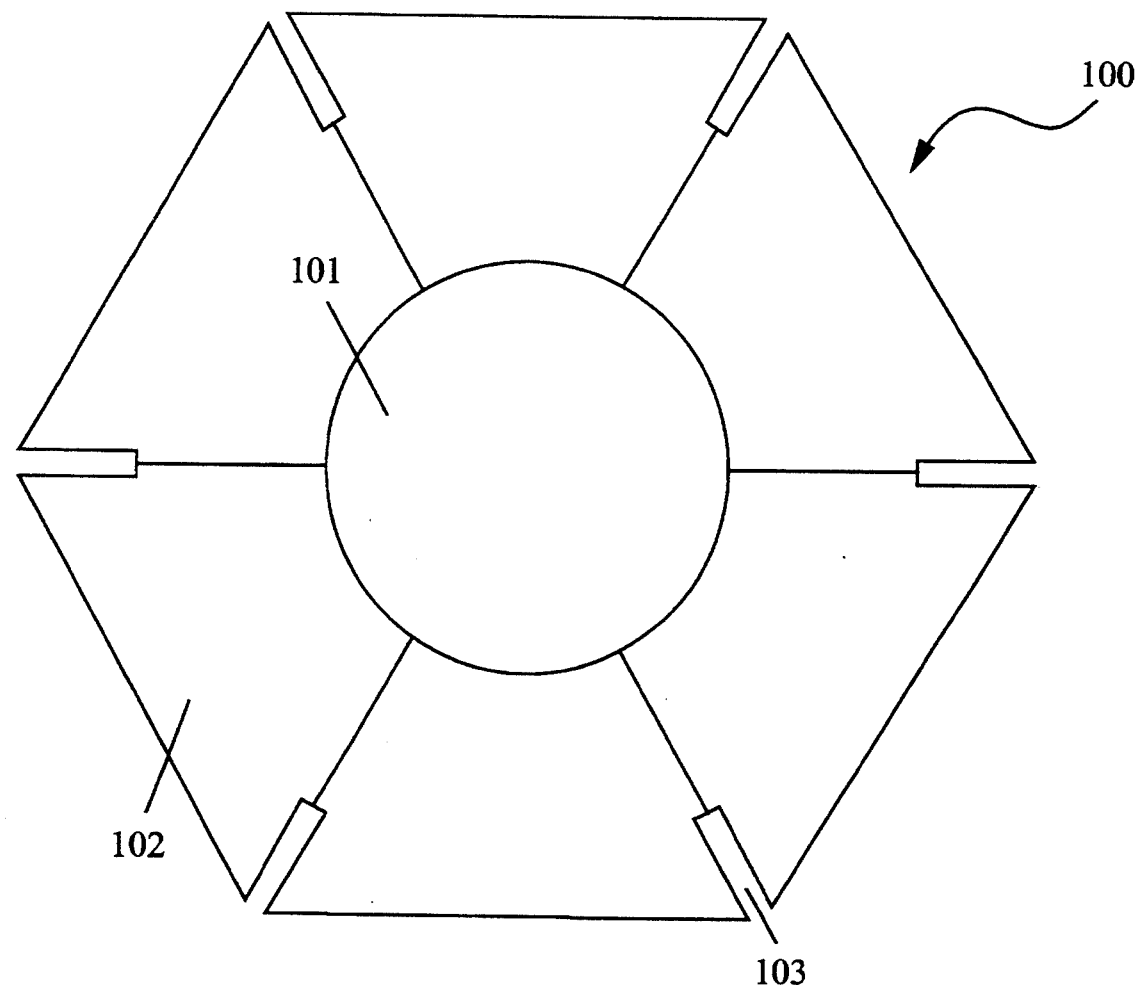
FIG. 1. shows a view of the preferred embodiment of the inspection device looking down directly at the viewing surface.

FIG. 1 shows the preferred embodiment of the present invention. The visual inspection device 100 of FIG. 1 is a six-sided polygon, however the number of sides would depend on the number of sample panels being used in the device. Corresponding to each side is a substantially flat sample panel 102. Each panel 102 is different with respect to one visual characteristic, but is otherwise exactly identical. For example, in one case the panels 102 are all the same color and material, but the surface texture of each one is different. The inspection device 100 also includes a viewing hole 101 which aids in making accurate comparisons between the various surface texture samples in the device and the manufactured article being inspected, as previously discussed. The embodiment of FIG. 1 also includes optional radial slots 103. These slots can be used to join a set of devices together for easy storage, or for joining an inspection device to the edge of another article to hold it in place.

Figure 2:
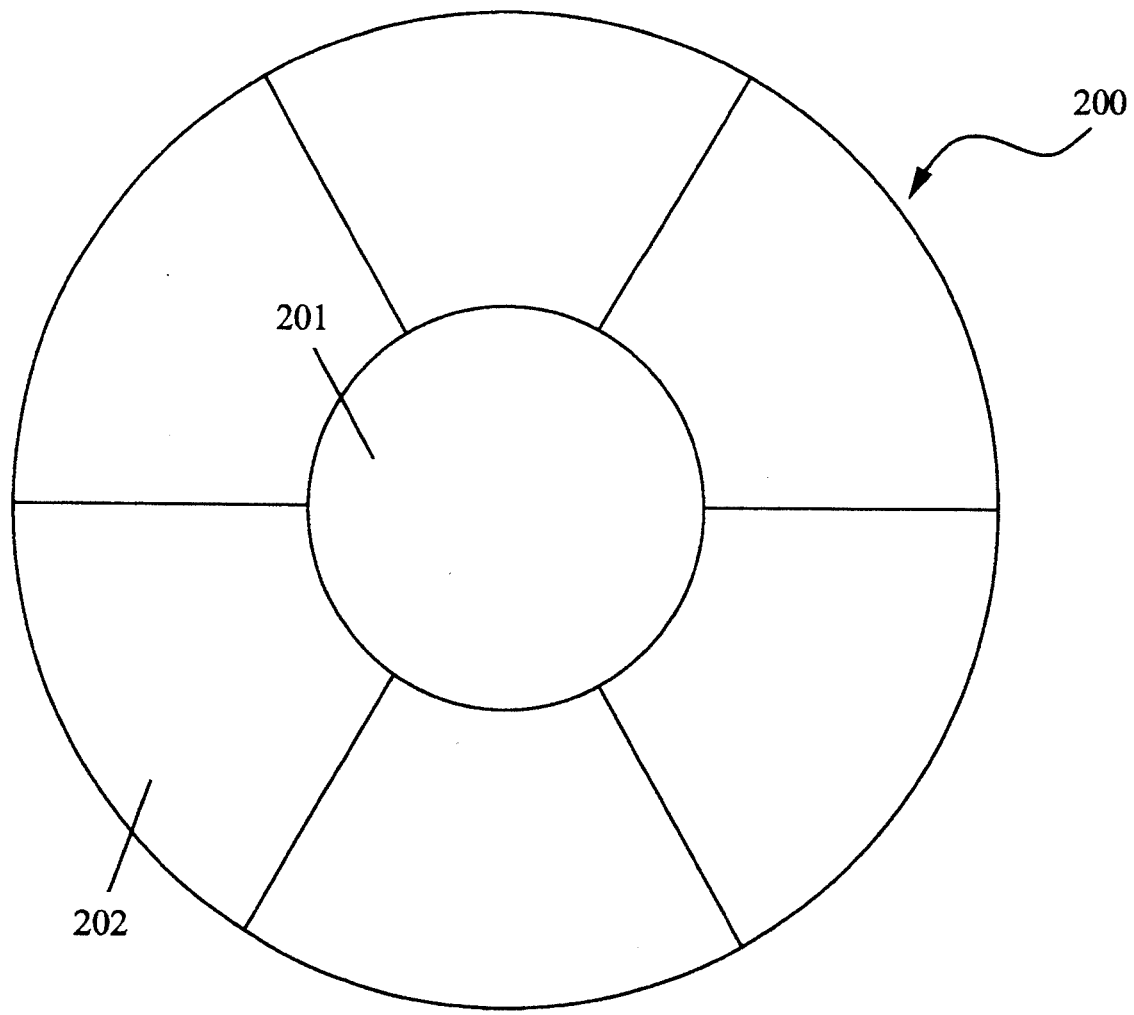
FIG. 2 shows an alternate embodiment of the device looking down at the viewing surface.

FIG. 2 shows an alternate embodiment of the inspection device. This device 200 is shaped like an annulus instead of a polygon. It has a sample panel 202 for each finish sample in the device and a viewing hole 201. Device 200 is pictured in FIG. 2 without the optional radial slots; however, an annular device can include the radial slots as well.

Figure 3:
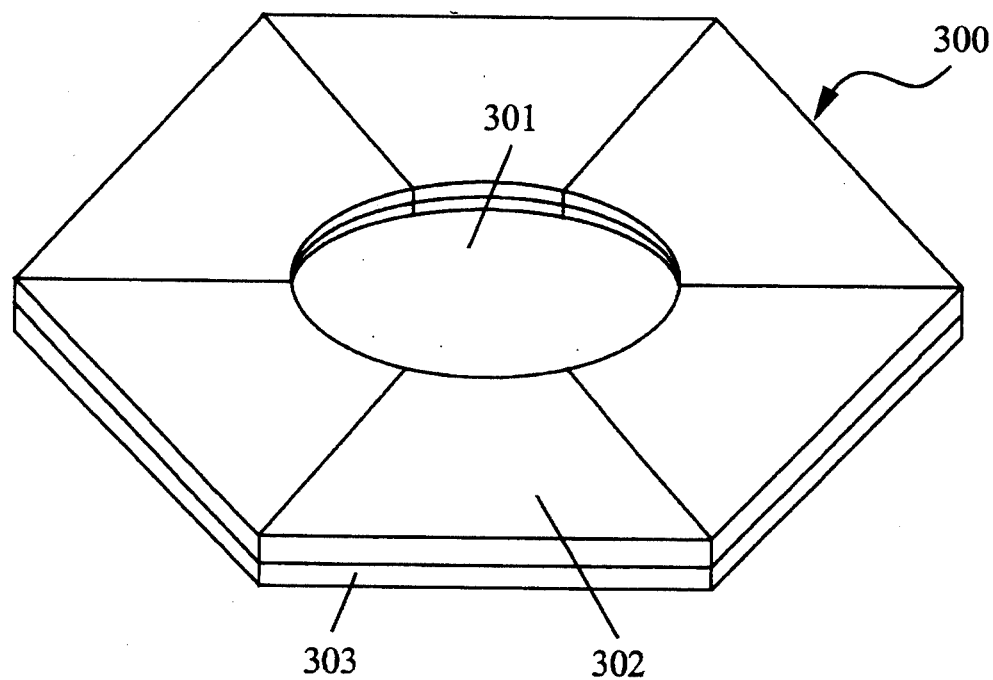
FIG. 3 shows an edgewise view of another embodiment in which the device is made by fastening finish sample panels onto a solid substrate.
Figure 4:
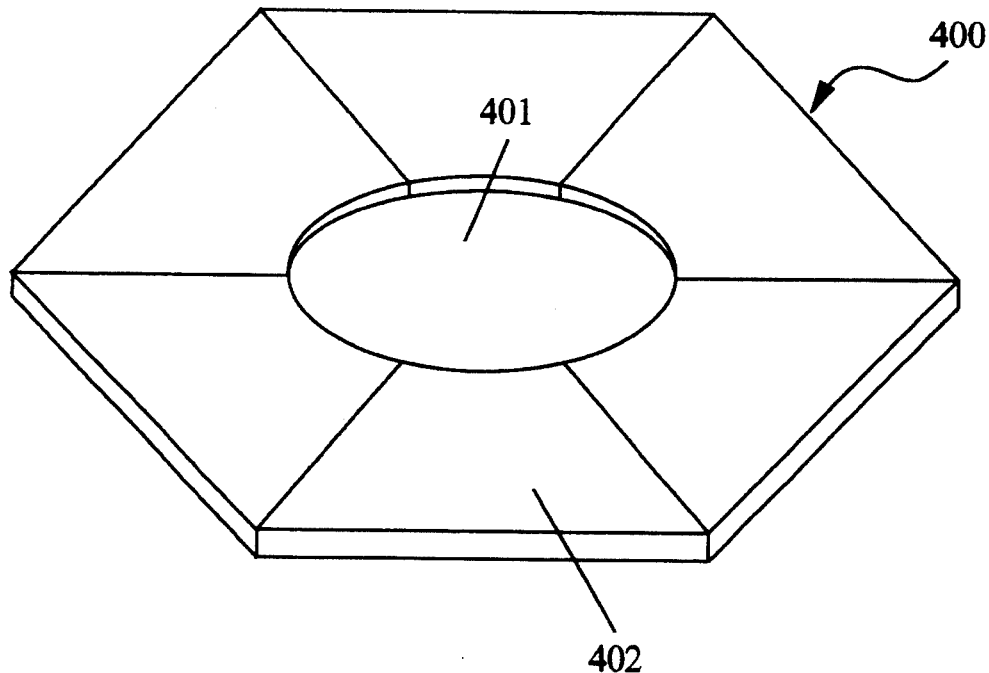
FIG. 4 shows an edgewise view of the inspection device made of a plurality of solid panels fixed together edgewise in which each panel is a completely separate piece of material.
Figure 5:
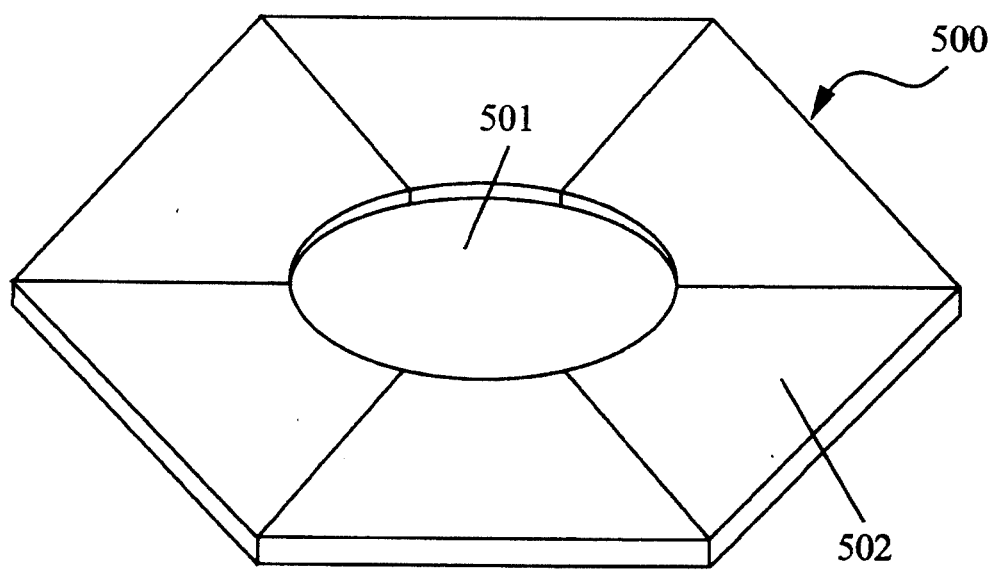
FIG. 5 shows an edgewise view of the inspection device made of a plurality of solid panels fixed together edgewise by making the inspection device from a solid piece of material.

FIG. 3, FIG. 4, and FIG. 5 show alternative ways of assembling the visual inspection device. Device 300 of FIG. 3 is assembled by affixing or fastening flat sample panels 302 to a solid substrate 303. The sample panels must be formed so they fit on the substrate precisely and allow a viewing hole 301 to remain unobstructed. The visual inspection device can be assembled in this way regardless of its shape. Device 300 is shown without the optional radial slots.

Device 400 of FIG. 4 is made up of solid panels 402 fixed together edgewise to form the inspection device. In device 400, the panels are actually separate pieces of material fixed together mechanically or with an adhesive. The panels are formed so that when they are assembled a viewing hole 401 is created. This method of assembly can be used for a device of any shape, as long as the panels are formed properly. Device 400 is shown without the optional radial slots.

Device 500 of FIG. 5 is also made up of solid panels fixed together edgewise to form the inspection device. In device 500, however, the panels are fixed together by forming them at once as one piece of material. Any injection molding process may be used. In this case, the panels are defined by scores 502 in the surface of the device. The scores 502, the viewing hole 501, and any necessary surface textures are produced by features of the mold used to make the device. Device 500 is shown without the optional radial slots, however any embodiment of the visual inspection device may be made with the radial slots.

The device is preferably used by holding it against the surface of a manufactured article and visually determining which of the samples in the inspection device is the closest match to the finish of the manufactured article. So that accurate inspections can be made, it is important that only one visual characteristic is varied from sample to sample in a single device. For example, if the finish texture of manufactured articles is being determined, the color of all the panels should be identical, and also should be the same as the color of the manufactured articles being inspected. For this reason, it is preferred to make all of the sample panels for a given device at the same time out of the same lot of material. In the case of inspecting finish texture, an inspector has on hand a set of inspection devices, each device being for use with a different color article. There would be one inspection device for every possible color finish to be inspected, and the samples in each device would each have a different texture, such as rough, semi-rough, gloss, etc.

The device could also be used to determine color. In this case there would be one inspection device for each possible finish material or finish texture, and each panel of a given device would be a different color. The same concept could be used to make inspection devices to determine other visual characteristics which can vary in the manufacturing process, such as reflectiveness or coarseness.

While annular and polygonal devices have been described, the polygonal shape is preferred because an inspector can hold it flat, edgewise against the side of a manufactured article to make determinations in addition to laying it down on an article and making use of the viewing hole. The inspection device could be made in other shapes, and with other variations, but the inventive concept is the same.

We claim:

1. A visual inspection device comprising:
   a substantially flat, substantially rigid, substantially disk-shaped substrate having a viewing hole in the center and a plurality of radial slots protruding partly into the substrate, the slots spaced evenly around the perimeter of the substrate; and
   a plurality of finish samples shaped so as to fit together edgewise adjacent to each other around the substrate while leaving the viewing hole and the slots open, the finish samples flatly affixed to the substrate, the visible surface of each sample having a different visual characteristic, the slots for fastening the inspection device to other objects.

2. The device of claim 1 wherein the visible surface color of each sample is the same and the visible surface texture of each sample is different.

3. A visual inspection device comprising:
   a plurality of substantially flat panels fixed together edgewise in the shape of a polygon, the panels fixed together edgewise to form a substantially flat, substantially rigid polygon having a viewing hole at the center, the device also having a plurality of radial slots protruding partly into the device, the slots spaced evenly around the perimeter of the device, the slots for fastening the inspection device to other objects, the visible surface of each panel having a different visual characteristic.

4. The device according to claim 3 wherein each panel has the same surface color and each panel has a different surface texture.

5. A visual inspection device comprising:
   a plurality of substantially flat panels fixed together edgewise in a substantially annular shape, the panels fixed together edgewise to form a substantially flat, substantially rigid body having a viewing hole at the center, the device also having a plurality of radial slots protruding partly into the device, the slots spaced evenly around the perimeter of the device, the slots for fastening the inspection device to other objects, the visible surface of each panel having a different visual characteristic.

6. The device according to claim 5 wherein the visible surface of each panel has the same surface color and has a different surface texture.

7. A visual inspection device comprising:
   a substantially flat, substantially rigid substrate have a plurality of sides so as the form a polygon, the substrate having a viewing hole in the center and a plurality of radial slots protruding partly into the substrate, the slots spaced evenly around the perimeter of the substrate; and a plurality of finish samples shaped so as to fit together edgewise adjacent to each other around the substrate, one sample per side, while leaving the viewing hole and the slots open, the samples flatly affixed to the substrate, the visible surface of each sample having a different visual characteristic, the slots for fastening the inspection device to other objects.

8. The device according to claim 7 wherein the visible surface of each sample has the same surface color and a different surface texture.

* * * * *